United States Patent [19]
Jones et al.

[11] Patent Number: 5,755,697
[45] Date of Patent: May 26, 1998

[54] SELF-TUNNELING, SELF-SECURING PERCUTANEOUS CATHETERIZATION DEVICE AND METHOD OF USE THEREOF

[76] Inventors: Calvin E. Jones, 14016 Greencroft La., Hunt Valley, Md. 21030-1108; Anthony J. Jescovitch, Jr., 1422 S. Charles St., Baltimore, Md. 21230

[21] Appl. No.: 562,051

[22] Filed: Nov. 22, 1995

[51] Int. Cl.$^6$ ..................................... A61M 5/32
[52] U.S. Cl. ............................. 604/174; 604/164
[58] Field of Search ..................... 609/264, 272, 609/158, 161, 164, 174, 175, 177

[56] References Cited

U.S. PATENT DOCUMENTS

| | | | |
|---|---|---|---|
| 4,425,118 | 1/1984 | Baumbach | 604/175 |
| 4,488,877 | 12/1984 | Klein et al. | 604/175 |
| 5,122,114 | 6/1992 | Miller et al. | 604/175 X |
| 5,122,122 | 6/1992 | Allgood | 604/174 |
| 5,147,316 | 9/1992 | Castillenti | 604/174 X |
| 5,226,890 | 7/1993 | Ianniruberto et al. | 604/174 X |
| 5,257,973 | 11/1993 | Villasuso | 604/175 X |
| 5,258,003 | 11/1993 | Ciaglia et al. | 604/164 X |
| 5,300,035 | 4/1994 | Clment | 604/175 X |
| 5,383,860 | 1/1995 | Lau | 604/164 X |
| 5,445,615 | 8/1995 | Yoon | 604/174 X |
| 5,478,329 | 12/1995 | Ternamian | 604/158 X |
| 5,512,053 | 4/1996 | Pearson et al. | 604/164 X |
| 5,591,191 | 1/1997 | Kieturakis | 604/164 X |

*Primary Examiner*—Sam Rimell

[57] ABSTRACT

This invention relates to a new and novel device to assist and improve percutaneous vein catheterization of patients. More particularly, this invention relates to a catheterization device which is self-tunneling, has a sleeve for protecting the catheter in the subcutaneous tissue beneath the puncture site, and has an annular skin cup for securing the device to the puncture site. This device allows a catheter to penetrate the skin without the need for a scalpel incision, development of a tunnel, or fluoroscopy, and is self secured to the patient, allowing sutures to be optional. The procedure for insertion of the device can be done in an inpatient or outpatient setting at the bedside by a trained physicians assistant, thereby providing access to the intended blood vessel without the necessity of a surgeon or operating room support.

Two embodiments of this new and novel device exist, one being a screw-type device and the other being a moly-type device. Both of these devices are bored along their longitudinal center and are used in conjunction with a internally fitting trocar.

16 Claims, 13 Drawing Sheets

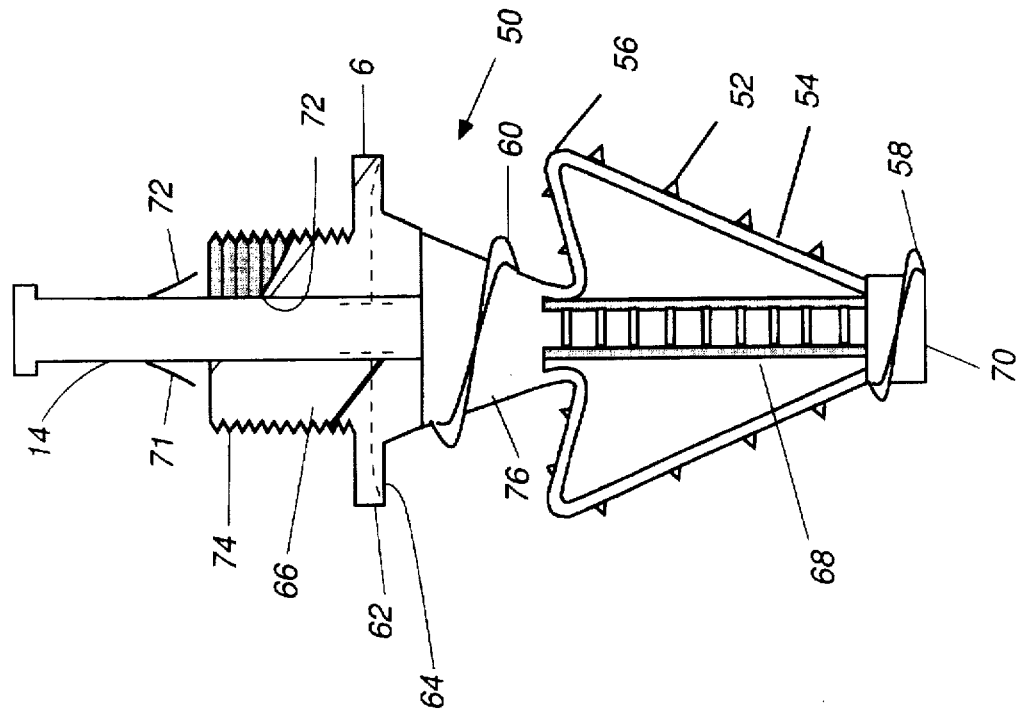
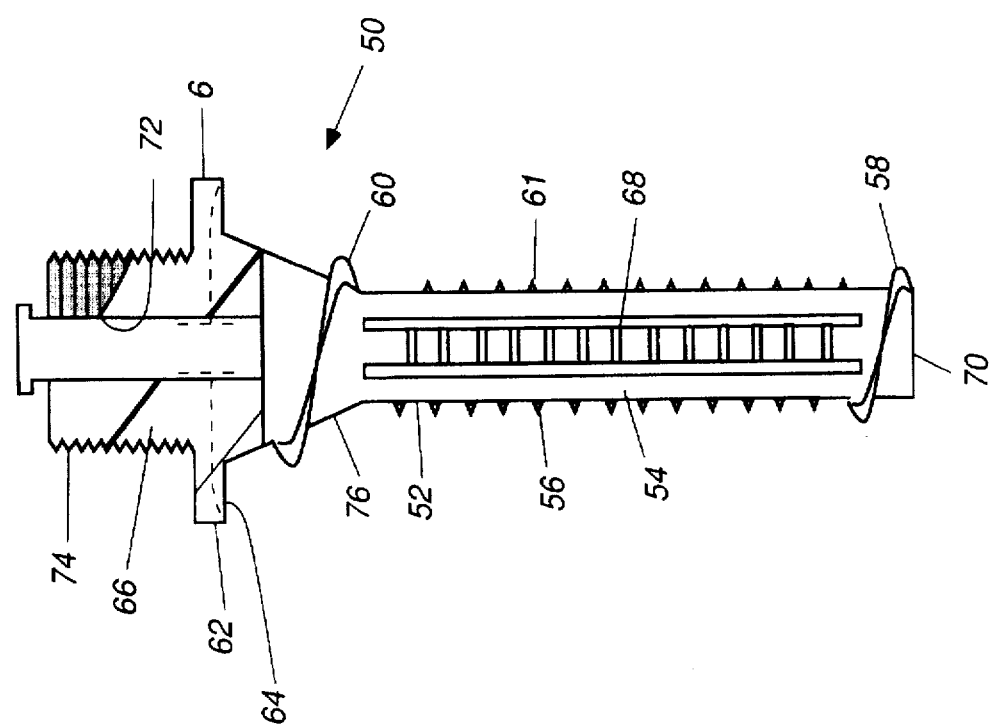

SELF-TUNNELING, SELF-SECURING PERCUTANEOUS CATHETERIZATION DEVICE AND METHOD OF USE THEREOF

BACKGROUND OF THE INVENTION

Introduction of fluids, medicinal or nutritional, directly into the vascular system is essential to the treatment and/or recovery of hospital patients. The fluids gain vascular access percutaneously through the common medical procedure termed catheterization. This procedure essentially uses a small tube, appropriately termed a catheter, as a conduit between an external source of treatment fluids and the patient's blood vessels. When properly inserted, the distal end of the catheter will reside within an appropriate vessel where an externally introduced fluid is carried and distributed to the body by the normal blood flow of the patient.

When catheterizing the central veins, a percutaneous catheter is introduced into the subclavian or innominate veins in the upper chest which joins the heart. A catheter can be inserted into these veins through a number of different body locations including the base of the neck, above or below the collar bone, the arm, the groin, or the back. The inserted and properly positioned catheter can then allow hemodynamic measurements to be made, blood samples to be obtained or externally introduce fluids into the bloodstream for subsequent distribution to the body within the normal blood flow of the patient.

Central venous access for hemodynamic monitoring, blood sampling, hemodialysis, and the introduction of fluids, medicines, blood and blood products or nutritional components into the central venous system is essential to the treatment of patients who may be hospitalized, in ambulatory chronic care facilities, or at home. This access may be employed for days, weeks or months for acute treatment, or for three months or greater if the usage is chronic.

When inserted for extended periods of time, the catheter or catheter track can become infected at the environmentally exposed skin puncture site where the catheter enters the body. Infections that may develop are typically not related to the initial insertion of the catheter as this procedure is performed under aseptic conditions. Instead, the infection probably develops as a result of the violation of the protective skin barrier and the long term exposure of the puncture site, through which the catheter gains access to the body, to external contaminants inherent in the environment and on the surface of the skin.

Tissue and catheter contamination is further exacerbated by the slight "to and fro" movement of the catheter in and out of the puncture site as a consequence of patient activity. This results in the externally exposed portion of the catheter moving inside the skin, thereby contaminating the clean subcutaneous tissue, while the sterile portion of the catheter in the body moves outside the puncture site, thus becoming contaminated.

This continuous "in and out" movement of the catheter results in tissue contamination that can precipitate local and/or systemic infection. When this happens, the catheter must be replaced at the same site or through a new site. Alleviating this predisposition for contamination would significantly benefit the patient by preventing local and potentially life threatening systemic sepsis, abrogate the need for catheter replacement and allow continued use of the same catheter and the same access site.

Typically, percutaneous central venous access for chronic usage is accomplished by a surgeon in the operating room. Anesthesia assistance to sedate the patient supplementing local anesthesia, especially when developing a tunnel, and fluoroscopic positioning of the catheter are are required.

A subcutaneous tunnel for the catheter begins at the skin puncture site, typically above the nipple, courses to the midpoint of the collar bone where another incision has been made at which site the catheter is introduced into the central vein and is properly positioned fluoroscopically. An instrument is placed through the tunnel from the puncture site just above the nipple to pull the opposite end of the catheter through the tunnel from the incision below the collar bone. The incision at the collar bone is then closed. Thus, the chronic catheter is a "U" configuration, entering the skin above the nipple and traversing straight up to the mid portion of the collar bone where it undergoes two 90° turns such that the tip of the catheter in the central vein is located approximately in the middle of the chest. Removing the catheter is as difficult a procedure as insertion and also will normally require operating room support.

Thus, catheterization, be it initial or replacement of the acute or chronic uses, is not only extremely inconvenient and uncomfortable for the patient, it can also become quite costly. Furthermore, the entire procedure may be painfully delayed by operating room and personnel scheduling conflicts.

What is needed to solve the problems associated with this necessary medical procedure is a tunneling sheath for both acute and chronic use that can be applied and removed at the bedside by non-surgeons, thereby abrogating the need for operating room, anesthesiology and fluoroscopy support. This type of device should effectively expedite the availability of access by allowing for easy application and maintenance. Furthermore, the new and novel device should secure the catheter to the patient and prevent in and out catheter movement, protect the catheter from environmental contact, protect the skin puncture site, and be functional under all circumstances without being being physically or socially obtrusive to the patient.

This present invention accommodates these and other considerations.

SUMMARY OF THE INVENTION

This invention relates to a new and novel device to assist and improve percutaneous vein catheterization of hospital patients. More particularly, this invention relates to a catheterization device which is self-tunneling, has a sleeve for protecting the catheter well into the subcutaneous tissue beneath the puncture site, and has an annular skin cup for securing the device to the puncture site. This device allows a catheter to penetrate the skin without the need for a scalpel incision, development of a tunnel, or fluoroscopy, and is self secured to the patient thus allowing sutures to be optional. The procedure for insertion of the device can be done in an inpatient or outpatient setting at the bedside by a trained physicians assistant, thereby providing access to the intended blood vessel without the necessity of a surgeon or operating room support.

This device, while novel in and of itself, is utilized in conjunction with the existing guide wire method of catheterization. Guide wire catheterization involves: (1) placing a needle within the proper blood vessel to be catheterized; (2) inserting a guide wire within the axial bore of the needle far enough to allow the distal end of the guide wire to additionally enter the blood vessel; (3) removing the needle by allowing it to slip over the guide wire, such that the guide wire remains in continuous communication with the interior of the blood vessel; (4) sliding a catheter over the guide wire so both the guide wire and catheter are within the blood vessel; and (5) removing the guide wire from within the catheter, again ensuring constant communication between the catheter and the blood vessel. The catheter is then typically sutured or adhesively secured to the surface of the skin.

The present invention improves upon this method by incorporating a self-tunnelling access device having a subcutaneous sleeve to protect the catheter from skin contamination and a flanged head to automatically secure the device to the patient without sutures or adhesive.

Two embodiments of this new and novel device exist, one being a screw-type device and the other being a moly-type device. Both of these devices are bored along their longitudinal center and are used in conjunction with an internally fitting trocar.

The trocar is used with both of these devices to start the threading process. The trocar fits snugly within the bores of these two devices and has a cutting blade at its distal end. To be operative, the trocar must be long enough to allow the cutting blade to extend outwardly past the distal end of the device such that the cutting blade can contact the skin. When the trocar is rotated, the cutting blade creates an aperture allowing the threads on the distal end of the device to catch and initiate screwing. At this time, the device is screwed into the skin until only the head is exposed on the exterior of the body, and the trocar removed.

The screw type device incorporates spiraling threads that function in the same manner as an ordinary wood or sheet metal screw. Since this device actually screws into the skin, it incidentally secures the device to the body in addition to imposing a subcutaneous tunnel which shields the catheter from puncture site contamination by the external environment.

The moly-type device is threaded at the extreme distal and proximal tunnel portions as well as intermittently threaded along its shaft so the device can also be initially screwed into the puncture site before securing the device to the surface of the skin with the moly joint. When the device has been inserted to a maximum depth, the moly joint is operated, displacing the movable sides within the body, forcing them to contact and rest against the interior layers of skin. Since the moly joint of the moly type device is the primary securing means, rather than the threads associated with the screw type device, the width of the threads on the moly device are substantially narrower than those incorporated on the screw type device.

Both of these devices are bored along their longitudinal center to facilitate insertion and removal of a catheter. Thus, when one of the two devices is installed and secured, a catheter can be inserted through it, into the blood vessel, and removed without any catheter contact at the puncture site or the subcutaneous tissue immediately beneath. Both of these devices are also coated with a tissue promoting substance, such as Dacron, along the shaft to enhance tissue growth around and on the device, creating a sterile and secure seal between the device and the skin of the catheterized patient thus protecting the catheter from environmental contamination which, until now, was unrealized by any method of percutaneous central venous catheterization.

It is therefore an object of this invention to provide an improvement to catheters that minimalizes entry site and surrounding tissue infections.

It is another object of this invention to provide a device that can self-start and self-tunnel into a patient so that a scalpel and incision is not needed to catheterize a patient.

It is a further object of this invention to reduce the cost to patients undergoing catheterizations by creating a device that allows in-patient or out-patient catheterization to take place at the bedside in a patient's room rather then in the operating room.

It is yet another object of this invention to provide a device that effectively prevents a catheter from moving "in and out" of the puncture site.

It is still a further object of this invention is to provide a device and method of catheterization that is easy to apply and maintain.

It is yet still a further object of this invention to provide a more sterile and comfortable method for long-term catheterization.

It is still another object of this invention to prevent a catheter from contacting subcutaneous tissue directly beneath the puncture site by having a tunneling portion of the device.

It is yet still another object of this invention to provide protection from environmental contaminants at the skin puncture site.

BRIEF DESCRIPTION OF THE DRAWINGS

The preceding and other intended objects, features and advantages of this invention will become more readily apparent from the following with reference to the accompanying drawings in which:

FIG. 9 is a partial longitudinal cross sectional illustration of the moly locking embodiment of the invention in insertion position.

FIG. 10 is a partial longitudinal cross sectional illustration of the moly locking embodiment of the invention of FIG. 9, shown in its operated or locked position.

DETAILED DESCRIPTION OF THE DRAWINGS

Figure 1:
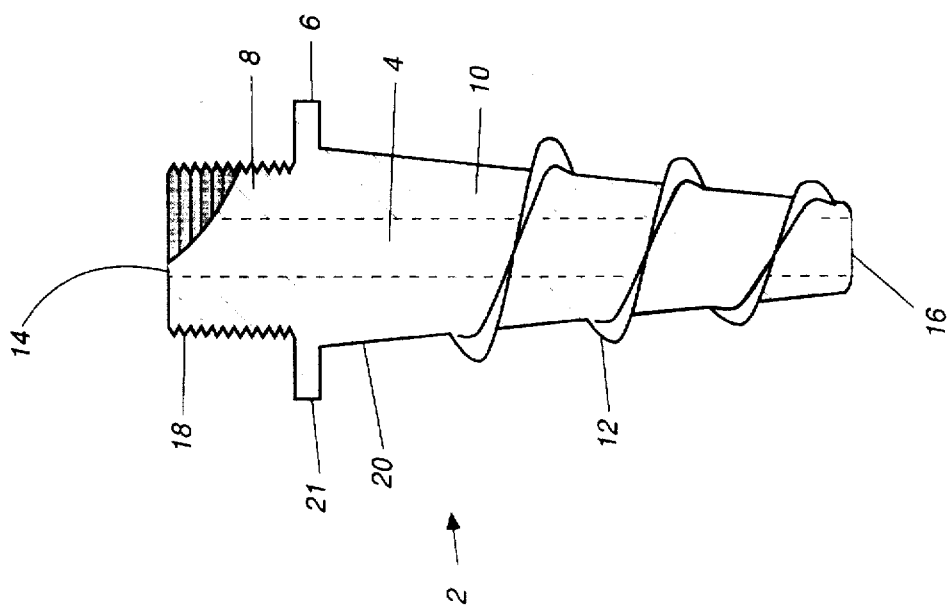
FIG. 1 is a partial longitudinal cross sectional illustration of the screwing embodiment of the invention.

Referring first to FIG. 1, the general embodiment of the screw type device 2 is depicted in partial longitudinal cross section. This device has two essential portions that are seamlessly incorporated, which advance and support the objects of this invention: (1) an external access port 8; and (2) a subcutaneous sleeve 10. The external access port 8 is substantially cylindrical and is circumferentially threaded 18 on its exterior surface. The subcutaneous sleeve 10 is substantially an inverted right circular cone, truncated near its intended vertex, and, like the access port 8, is also threaded 12 about its outer face. The diameters of the base of the subcutaneous sleeve 10 and the access port 8, respectively, are substantially equal, making a retaining ring 6 necessary to prevent the device from being fully or overly inserted into the body.

The retaining ring is an annular skin cup 6, separating the two different portions of the screw device 2. The annular skin cup 6 is preferably twice the diameter of the cylindrical access port 8, providing a sufficient retaining area in relation to the size of the puncture site ensuring that over-insertion will not occur and additionally providing the inserted screw device 2 with stability, thereby reducing incidental movement.

The annular skin cup 6 has a concave portion 20 on the face that contacts the outer surface of the skin. This allows the device 2 to be screwed deeper into the skin of a patient than the outer radial rim 21 of the annular cup 6 would allow if the skin was not pliable, creating a tighter seal than if the contacting face of the annular skin cup 6 was flat and planular.

Preferably, the threads on the external access port 8 and the subcutaneous sleeve 10 differ in helical spacing in order to facilitate their differing functions. The fine threading 18 on the access port 8 is necessary for a tight connection to a cap (typically and generally shown in FIG. 17). The numerous threads 18 create a tighter seal preventing contaminants from violating this connection. The courser threads 12 spirally incorporated on the outer face of the subcutaneous sleeve 10 are necessary for quick and efficient skin penetration.

Sealing the device to the skin is not primarily accomplished by the threads themselves, which allows for the courser helical spacing. Sealing the device to the puncture site is integrally accomplished by the natural tendency of the skin to retract when stretched by the intrusive device at the puncture site and the concave annular skin cup. To further enhance the integrity of this seal, the subcutaneous portions of the device, except for the cutting threads 12 themselves, are coated with a tissue promoting substance, such as Dacron, fostering tissue growth along, around, and to the device.

The screw-type device is also bored 4 longitudinally through its center, with an entrance 14 located on the external access port 8 and an exit 16 located at the distal, truncated end of the subcutaneous sleeve 10. This bore 4 is essential in fulfilling the intended purpose of this invention as it is the percutaneous conduit which is used to house the catheter and thereby shield it from environmental contaminants. The central bore 4 additionally serves as the temporary chamber for the threaded trocar 22, illustrated in FIG. 2, when the device 2 is initially inserted into the body of the patient. Since the subcutaneous sleeve 10 is truncated at its distal end to create an exit orifice for a catheter, the threads 12 do not have a starting point and the device can not penetrate the skin without using the threaded trocar 22.

The trocar 22 has three essential portions: (1) a central body shaft 34; (2) a handle 26; and (3) a cutting means 32. The shaft 34 of the trocar 22 fits snugly within the central bore 10 of the screw device 2, preventing any transverse movement while still allowing for longitudinal rotation. The trocar 22 is slightly longer than the central bore 4 of the screw-type device 2 so that when inserted, the cutting means 32 provided on the distal end 30 of the trocar 22 extends outwardly beyond the exit orifice 16 of the subcutaneous sleeve 10.

At one end of the shaft 34, the trocar has a stop 24 and a handle 26. The stop 24 is a short cylindrical section, larger in diameter than the central bore 4 in the screw device 2, preventing insertion of the trocar 22 further than the stop 24. Extending radially from the stop, at a portion of the stop 24 which is furthest away from the shaft 34, is a handle 26. The handle 26 facilitates controlled rotation of the trocar 22 as well as providing a location, perpendicular to the shaft 34, for applying gentle pressure to the trocar 22 when penetrating the skin.

The distal end 30 of the trocar 22 is equipped with a cutting means 32, such as a small blade, drill bit tip, or threads spiraling helically into a sharp puncturing point. Since the cutting means 32 extends beyond the end of the subcutaneous sleeve 10, it contacts and increasingly punctures the skin, thereby creating a sufficient opening to initiate independent threading of the subcutaneous threaded sleeve 10. The portion of the shaft 34 which extends outwardly beyond the central bore 10 of the screw device 2 is tapered proportionally to the conical shape of the subcutaneous sleeve 10 and, when the trocar 22 is inserted into the screw device 2, actually transforms the truncated cone into a full completed cone with its vertex being the extreme distal tip 30 of the trocar 22.

The trocar 22 also has a central bore 28 through its complete longitudinal length. This bore 28 allows the trocar 22 to be slipped over a guide wire during the catheterization procedure as this device 2 is intended to be inserted using the "over the wire" catheterization method well known in the art.

Figure 3:
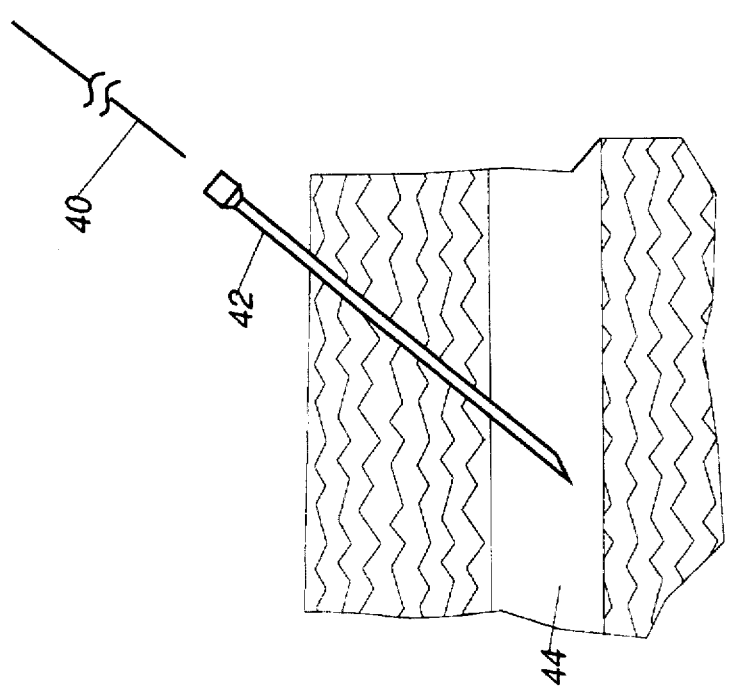

This method, used in conjunction with the present invention, is illustratively performed in FIGS. 3–8. Referring first to FIG. 3, the process begins with percutaneous needle 42 cannulation of the intended blood vessel 44. A guide wire 40 is sufficiently inserted through the needle until it exits into the vessel 44. The needle is then carefully retracted from the body by sliding over the guide wire 40 until it is completely removed.

Figure 4:
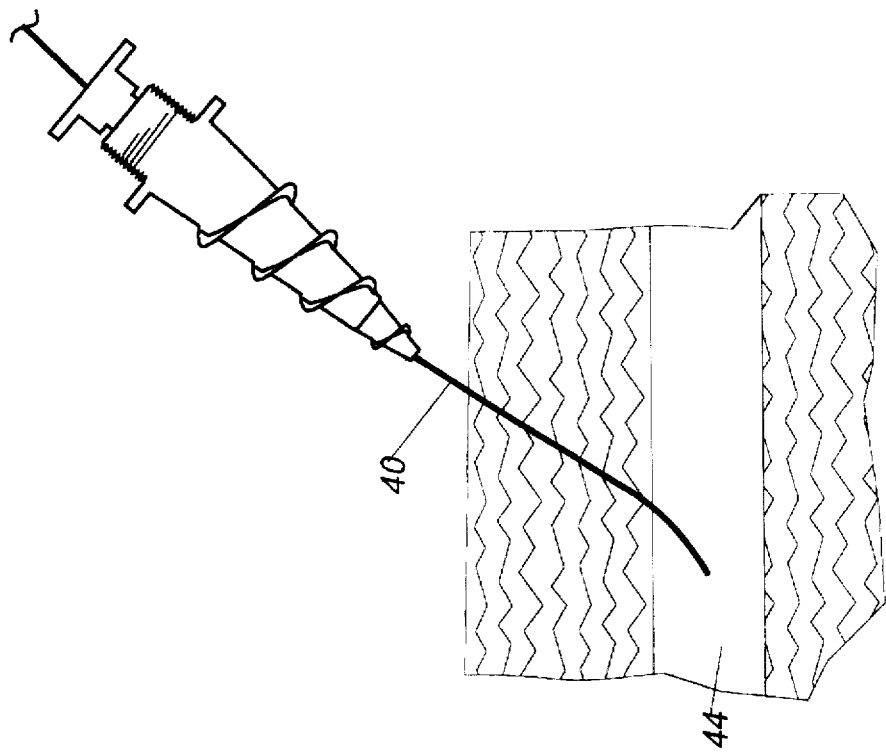
FIGS. 3 through 8 pictorially illustrate the procedure for utilizing the screw-type device of FIG. 1 to catheterize a patient.
Figure 6:
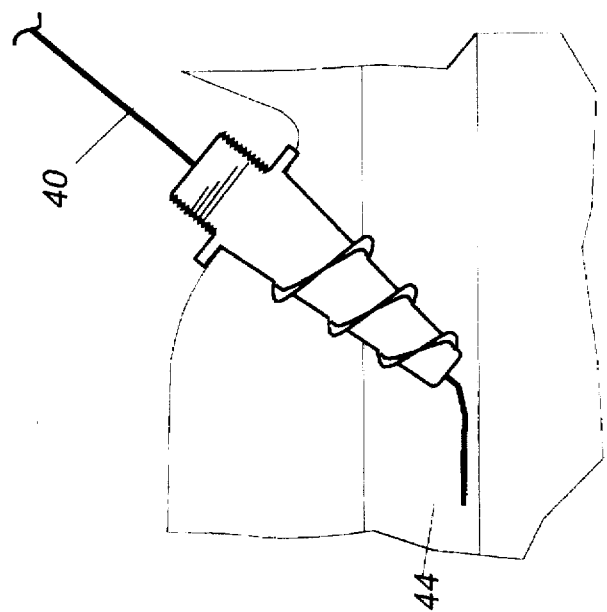
Figure 5:
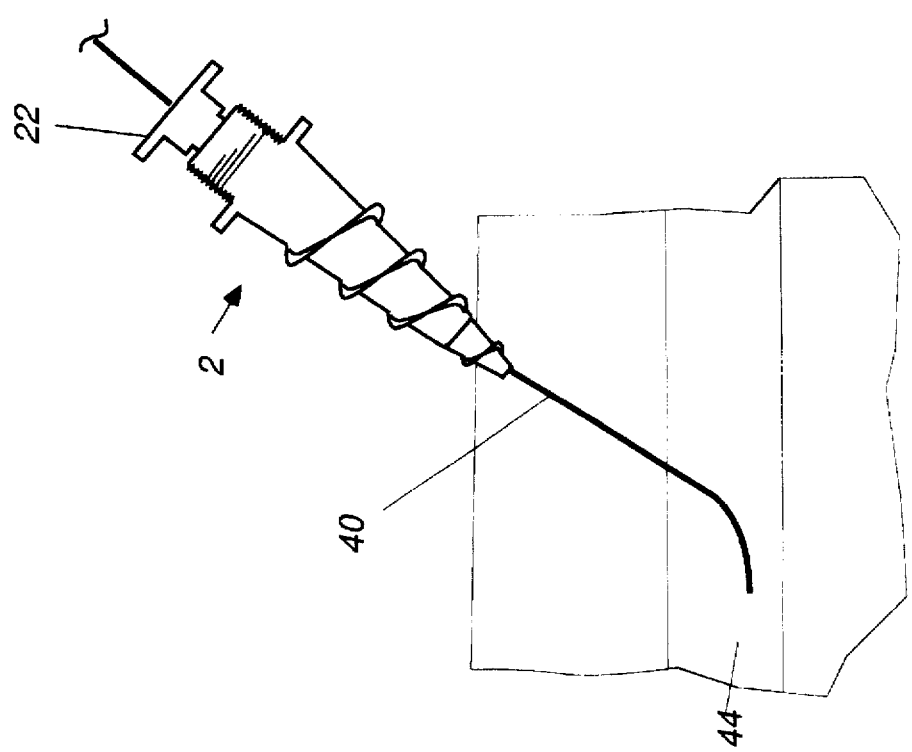

The guide wire 40 is retained within the vessel 44 intended to be catheterized as seen in FIG. 4. The screw device 2, with the trocar 22 inserted within it, is inserted onto the guide wire 40 through the central bore 28 in the trocar 22. Once the screw device rests on the surface of the skin 46, slight pressure is applied and the trocar 22 is rotated in the direction which promotes cutting or piercing of the skin by the cutting means 32. As the skin rides up and over the trocar 22 onto the subcutaneous sleeve 10, the device 2 is rotated as the threads 12 increasingly embed the device 2 within the body as shown in FIG. 5. Rotation continues until the skin is firmly abutted against the concave face 20 of the annular skin cup 6 as seen in FIG. 6.

Figure 8:
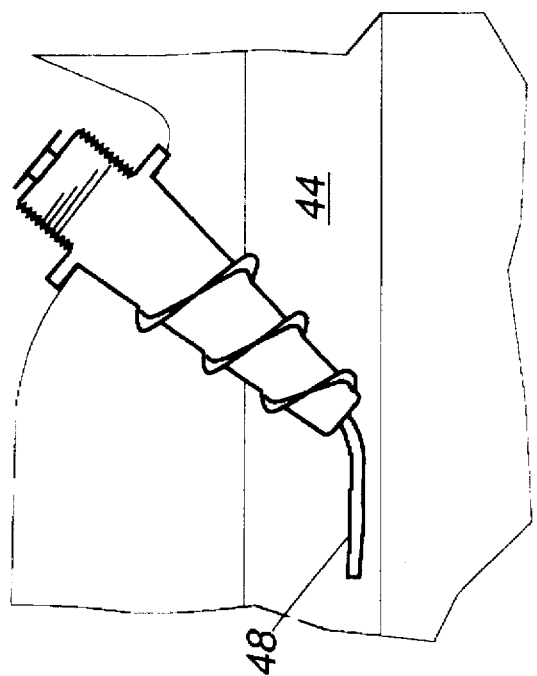
Figure 7:
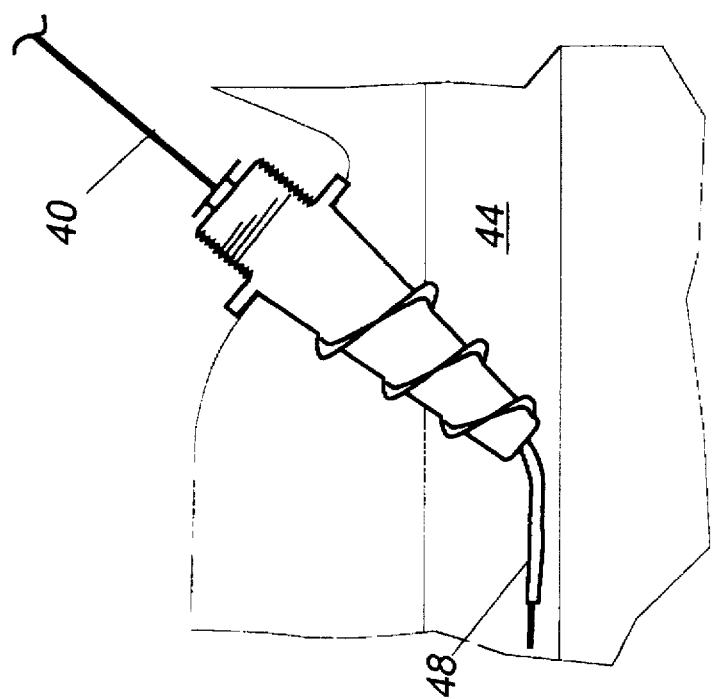
Figure 12:
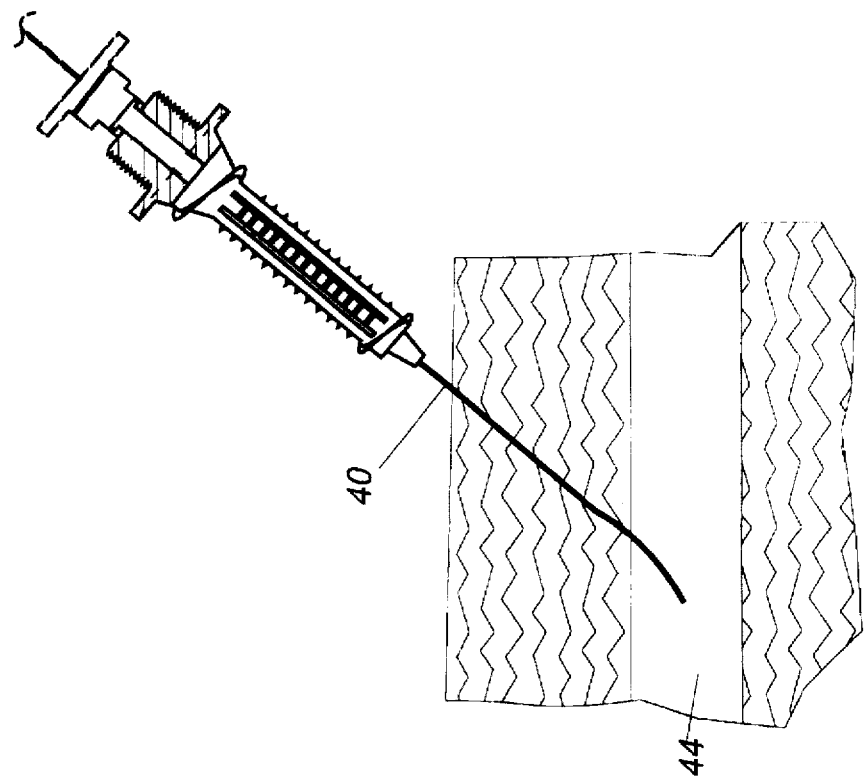
FIGS. 11 through 16 pictorially illustrate the procedure for utilizing the moly-type device of FIGS. 9 and 10 to catheterize a patient.

Once the subcutaneous sleeve is firmly embedded within the patient, the trocar is removed and a vessel dilator is inserted over the guide wire 40 into the blood vessel 44 and then removed. A catheter 48, of appropriate diameter, is then threaded over the guide wire 40, through the screw-type device 2 and into the blood vessel 44 and the guide wire 40 is carefully removed, as seen in FIGS. 7 and 8. Access is now complete and the device (2) now merely needs to be connected to an external fluid source.

The second embodiment of the present invention works in substantially the same manner as the first embodiment, differing merely in the means for securing and sealing the device within the body of the patient to be catheterized.

Generally, the second embodiment is a moly-type device 50 and is illustrated in its inserted position and its locked position in FIGS. 9 and 10, respectively. The moly device 50, as with the screw device 2, is comprised of an external access port 66, threaded 74 to accept a cap or external lumen connection (typically and generally shown in FIGS. 19 and 23A, respectively). The annular skin cup 62 and concave portion 64 discussed above with respect to the screw device 2 are also present in this second embodiment, serving identical functions.

This embodiment, however, differs in that it does not have an elongated subcutaneous conical sleeve 10 (FIG. 1), but instead has a compressed conical sleeve 76, substantially shorter in length in relation to that of the screw device 2. The elongated sleeve 10 is not necessary in this embodiment because the moly joint secures the device 50 to the skin rather than the combination of threading and skin tension utilized by the screw device 2.

The moly joint works in a similar manner to that of an ordinary moly-type hollow wall bolt, having two pairs of opposed moly members each being comprised of two rigid members 52, 54 and a flexible connecting joint 56. Preferably, this joint will be fabricated from either a single flexible plastic member or a single flexible stainless steel member, being scored in an appropriate area to create the flexible, inwardly folding joint 56.

The moly joints 52, 54, 56 are connected at one end 52 to the compressed subcutaneous sleeve 76 and at the other 54 to the distal portion 70 of the central shaft 68. The shaft 68 resides within a central bore 72 that runs axially through the access port 66, the annular skin cup 62, and the compressed subcutaneous sleeve 76. The shaft 68 is not immovably fixed to any of these three parts and is sized appropriately with respect to the central bore 72 to allow for sliding movement.

Sliding the central shaft 68 outward forces moly joint members 52 and 54 to operate, bringing member 52 towards the subcutaneous surface of the skin, which secures the device 50 from release and reduces incidental movement. Two small latches 71 are attached to the periphery of the shaft 68 and are deformed in such a way that they have a perpetual tendency to spring outward. These latches 71, when allowed to spring outward by extracting the shaft 68 fully, lock the shaft 68 and the moly joint in place. The shaft 68 can then only be released and reinserted within the bore 72 by placing hand pressure against the latches 71 so that they lay tangential to the central shaft 68, allowing them to be inserted within the bore 72.

Figure 19:
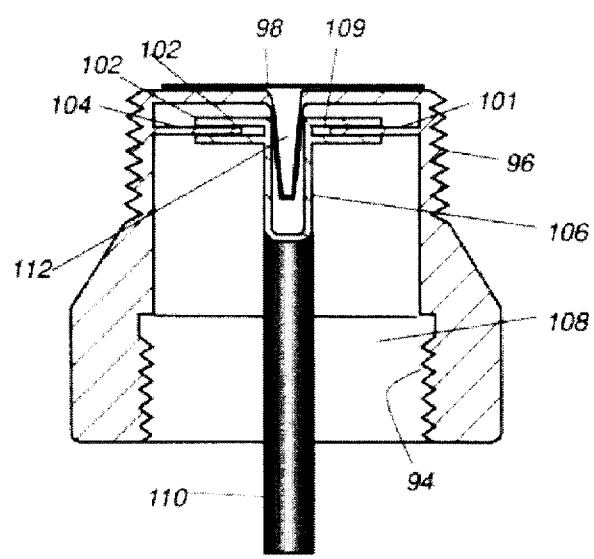
FIG. 19 is a longitudinal cross section of a typical cap to be used in conjunction with the moly-type device of FIGS. 9 and 10, specifically illustrating the extended portion which is necessary to accommodate the central shaft when the moly device is in locked position.

The shaft 68 has a rimed proximal end 69 which serves two purposes. First, it acts as a handle when extracting or retracting the shaft 68 when operating the moly joint. The rim 69 must therefore reside, when the moly device 50 is in insertion position (FIG. 9), far enough above the top face of the access port 66 to allow it to be easily grasped. Second, the rim 69 acts as an "O" ring sealer when the cap illustrated in FIG. 19 is attached, by butting against an inner flange incorporated within the cap.

Figure 2:
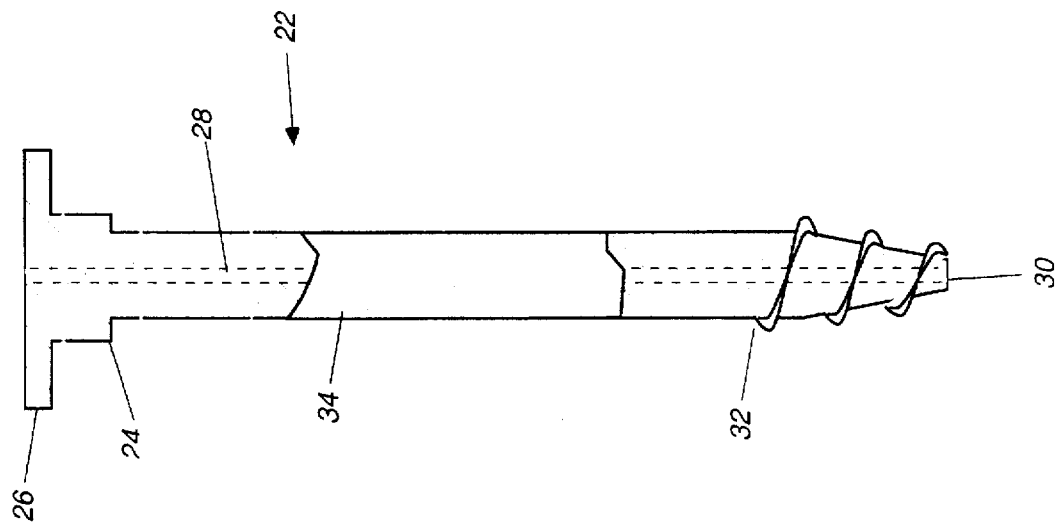
FIG. 2 is a partial longitudinal cross sectional illustration of the trocar utilized during the insertion of the screw-type device of FIG. 1 and the moly type device of FIGS. 9 and 10.

Even though the moly device does not use threads for securing itself, it has a band of threads below 58 and above 60 the moly joint 52, 54, 56 as well as intermittent threads 61 along the moly joint to assist with insertion. In order to start the threads incorporated on the device 50, the moly device 50 must also be inserted with the assistance of a trocar 22, the same as illustrated in FIG. 2, and the central shaft 68 of the moly device 50 is therefore of a sufficient diameter to rotatably house the trocar 22. The threads 58 below the moly joint 52, 54, 56, assure that the puncture orifice in the skin, initiated by the tapered end of the trocar 22, is sufficiently large enough to allow the intermittent threads 61 along the moly joint 52, 54, 56 to be continuously threaded therethrough.

Once the compressed subcutaneous sleeve 76 contacts the puncture site, rotation is continued to allow the threads 60 on the compressed sleeve 76 to increasingly insert the device fully into the puncture site. These threads 60 are necessary to support the device in the body while the moly joint 52, 54, 56 is operated and extended, thereby securing the moly device 50 for long term placement. Furthermore, these threads 60 displace the skin upwardly within the concave portion 64 of the annular skin cap 62, sealing the puncture site from any external contaminants.

Figure 11:
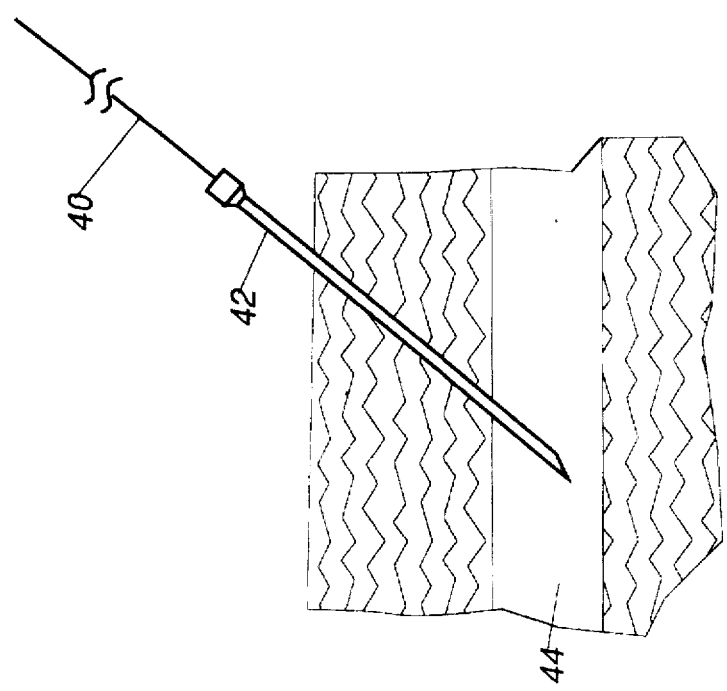

The process for catheterization when using the moly device 50 is illustratively performed in FIGS. 11 to 16. This process, which is very similar to that described above for the screw device, is also used in conjunction with the traditional "over the wire" catheterization method. FIG. 11 illustrates percutaneous needle 42 cannulation of the appropriate vein, the initial step in the process. A guide wire 40 is inserted through the needle 42, into the blood vessel 44, and then the needle 42 is carefully retracted while leaving the guide wire 40 within the blood vessel 44. This is clearly illustrated in FIG. 12.

Figure 14:
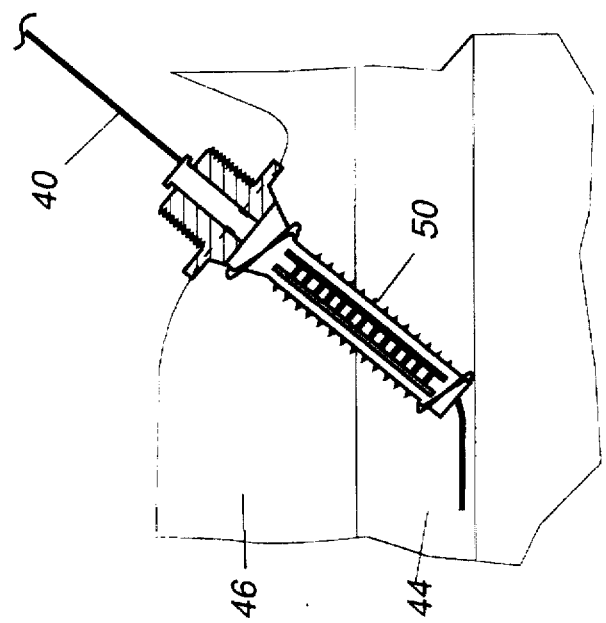
Figure 13:
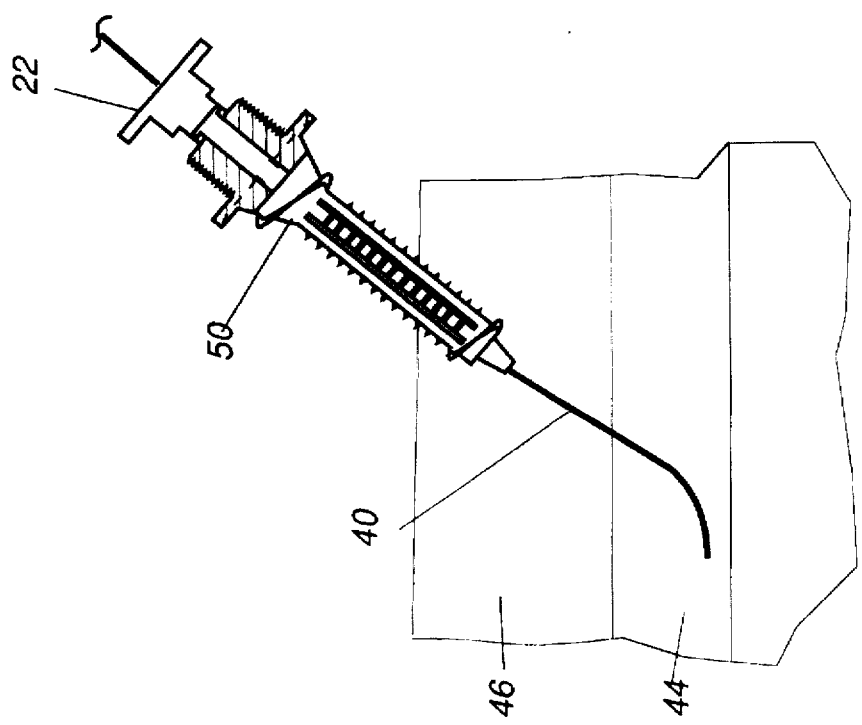

A moly device 50, housing a trocar 22, is inserted over the guide wire 40 until the trocar 22 contacts and punctures the skin. The trocar 22 dilates the puncture site, allowing the moly device 50 to be inserted by constant rotation of the threads until the puncture site contacts the annular skin cup, as seen in FIGS. 13 and 14.

Figure 16:
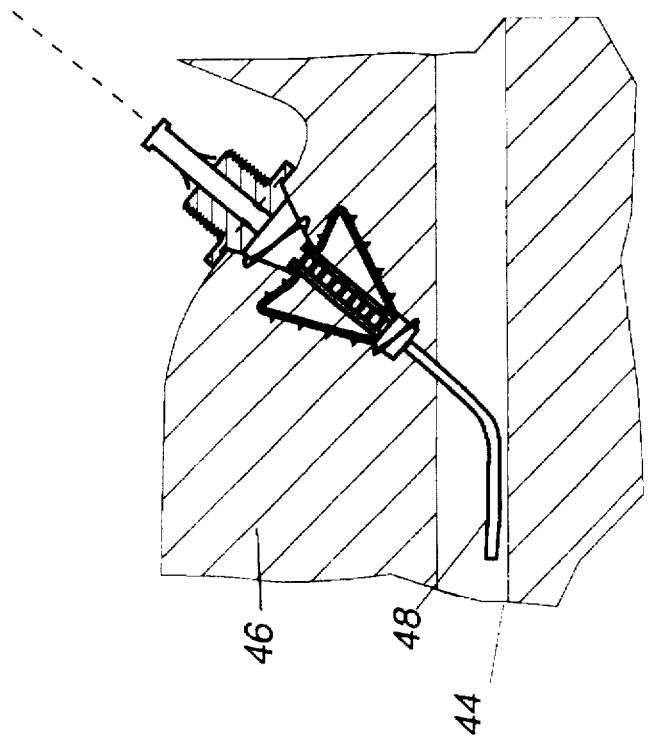
Figure 15:
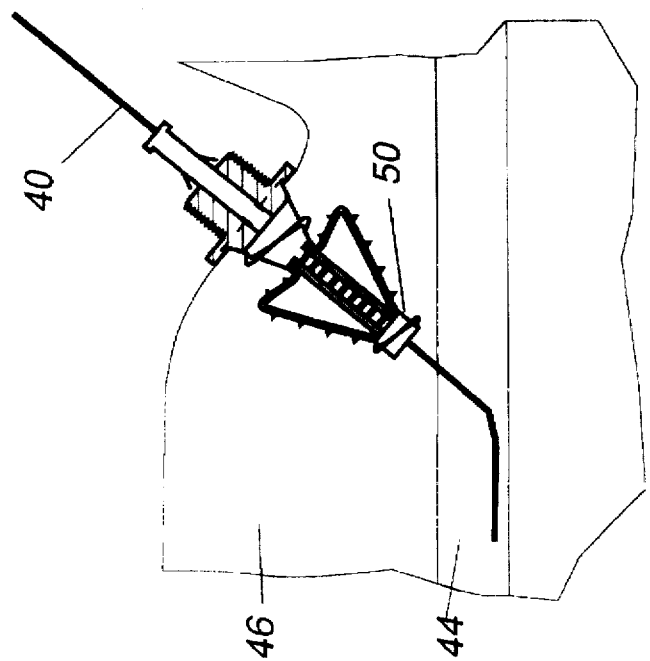

The trocar 22 is now removed, as seen in FIGS. 15 and 16, and the moly joint 50 is toggled into its locked position. An appropriately sized catheter 48 is then threaded over the guide wire 40 until it is sufficiently within the blood vessel 44 and the guide wire is carefully removed as seen in FIGS. 15 and 16. At this point, the catheter device is secured by an appropriate connecting piece attached to the access port.

Figure 17:
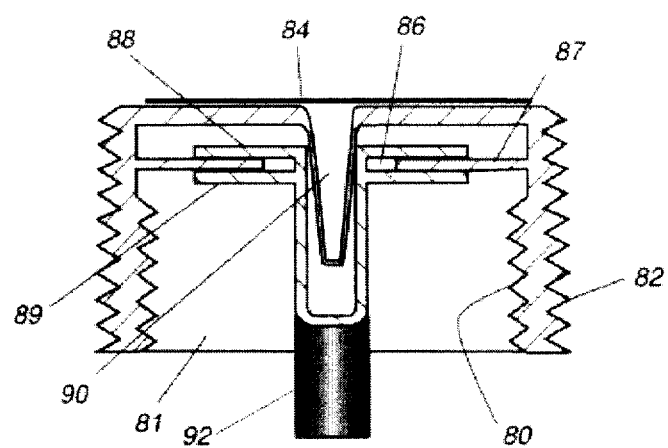
FIG. 17 is a longitudinal cross section of a typical cap to be used in conjunction with the screw-type device of FIG. 1.

Several connections to both the screw 2 and moly 50 device are possible as the access port of each can be threadingly engaged by any appropriately sized internally threaded female attachment. Referring now to FIGS. 17 and 19, typical attachments for the screw device and the moly device, respectively, are disclosed.

While differing in physical embodiment, these caps each have similar components which serve similar functions. Integral to both caps are an external and internal set of threads. Still referring to FIGS. 17 and 19 (respectively where dual reference numbers appear) the internal threads 80, 94 are located on the periphery of the female connecting chamber 81, 108. These threads 80, 94 are appropriately situated, sized, and aligned to rotatingly thread onto the screw 2 and moly devices 50. The external threads 82, 96 are appropriately sized to accept a connection device, such as that seen in FIG. 21.

Extending from the bottom of each cap is an internal catheter 92, 110 to be inserted within the body of a patient who already has a screw 2 or moly 50 device inserted. The catheter 92, 110 is rotatably attached to the cap such that the internal threads 80, 94 can be fastened by rotation without rotating the catheter 92, 110 which will already be inserted in the body. One way independent rotation can be accomplished is by utilizing double flanged catheter ends 88, 102, with each flange residing on one side of an orifice 86, 109 located in a rigid cross section 87, 101 of the cap.

Above the orifice 86, 109 is a puncturable rubber membrane 84, 98 separating the catheter opening at the double flanged end 86, 109 from the environment. The rubber membrane 84, 98 has a rigid plastic truncated conical insert 90, 112 molded therebeneath, assuring that fluids which traverse the pierced membrane 84, 98 go into the catheter 92, 110. The rubber membrane 84, 98 and rigid cone insert 90, 112 combination is commonly used with catheter connections as the membrane 84, 98 is self-sealing upon removal of a puncturing means.

Figure 18:
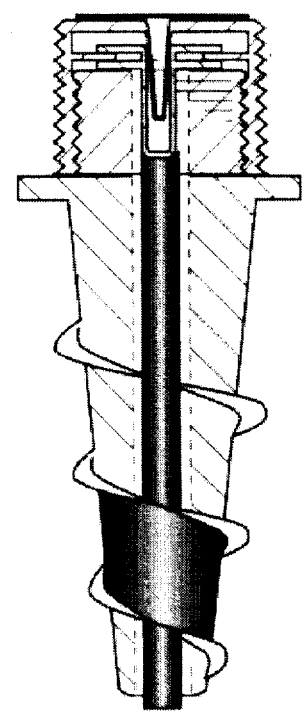
FIG. 18 shows the cap of FIG. 17 fastened to the screw-type device of FIG. 1.
Figure 20:
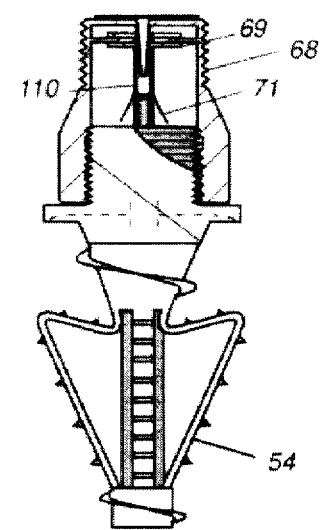
FIG. 20 shows the cap of FIG. 19 fastened to the moly-type device of FIGS. 9 and 10.

As seen in FIGS. 18 and 20, these caps fit onto the respective access ports 8, 66 of the screw and moly devices. This is where the cap of FIG. 17 differs from the cap of FIG. 19. The cap of FIG. 19, for the moly device 50, must have a cavity 108 to accept the outwardly extending central shaft 68 when in locked position.

Both caps intentionally do not thread all the way down to the skin access cups 8, 66. Rather, threading will stop when the lower flange 89, 104 of catheter 92, 110 contacts the top of the access port 8 for the screw device, or the flanged rim 69 of the central shaft 68 for the moly device 50. The integrity of either seal can additionally be improved by placing silicon "O" rings at the point of contact between the lower flange 89, 104 and the access port 8 of the screw device 2 or the upper rim 69 of the moly device 50. Besides creating a tight seal, the pressure on the bottom flange 89, 104 of the catheter 92, 110 presses it firmly against the rigid cross section 87, 101 of the cap, thereby causing any independent rotation to cease, as well as preventing the cap from unintentional loosening.

When capped, the access device and internal catheter 92, 110 can remain in the body until access to a blood vessel is necessary, in which case a puncturing means must be used to violate the rubber membrane 84, 98, allowing access to the blood stream.

The simplest way to puncture the membrane 84, 98 and introduce alien fluids into the blood stream is by syringe. A syringe can be inserted through the membrane 84, 98 and discharged into the internal catheter 92, 110, which takes the discharged fluid to the blood vessel. When the syringe is removed, the rubber membrane 84, 98 will seal itself, allowing the catheter to remain inserted until a later treatment is necessary. While using a syringe to introduce fluids using the device is convenient, it is not practical when large or frequent doses of fluids are necessary. A attachment to the device for this situation is necessary.

Figure 21:
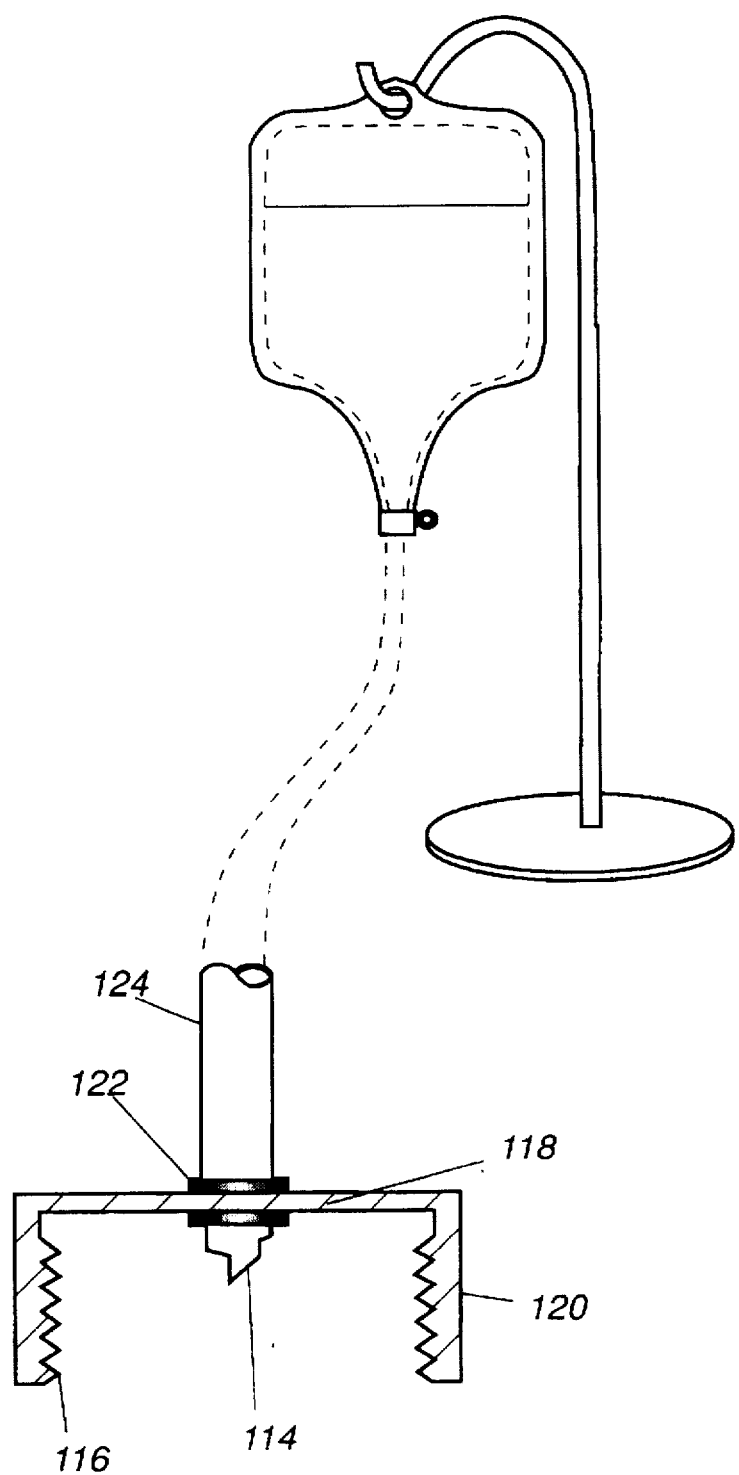
FIG. 21 shows a safety piercing attachment used with either the cap of FIG. 17 or FIG. 19 connected to a typical medicinal container.

Referring to FIG. 21, a typical piercing attachment is shown which will give continuous access to the blood vessel when large or frequent treatments are necessary. The attachment includes a piercing means 114 to penetrate the rubber membrane 84, 98 and a set of threads 116 on the interior of the rotatable cap attachment 120 to rotationally engage the threads 82, 96 of the female connecting chamber 81, 108. The piercing means 114 should be independently rotatable from the threaded portion 116, such that the threaded portion 116 can be threaded to the cap without rotating the piecing means 114 or the lumen 124 attached thereto. This again can be simply accomplished by a double flanged attachment 122 similar to that used for the internal catheters illustrated in FIGS. 17 and 19. The lumen 124 is connected to a typical medicine bag or other fluid container which will feed into the catheterized blood vessel when the piercing attachment, the cap, and the access device are all correctly connected.

Figure 22:
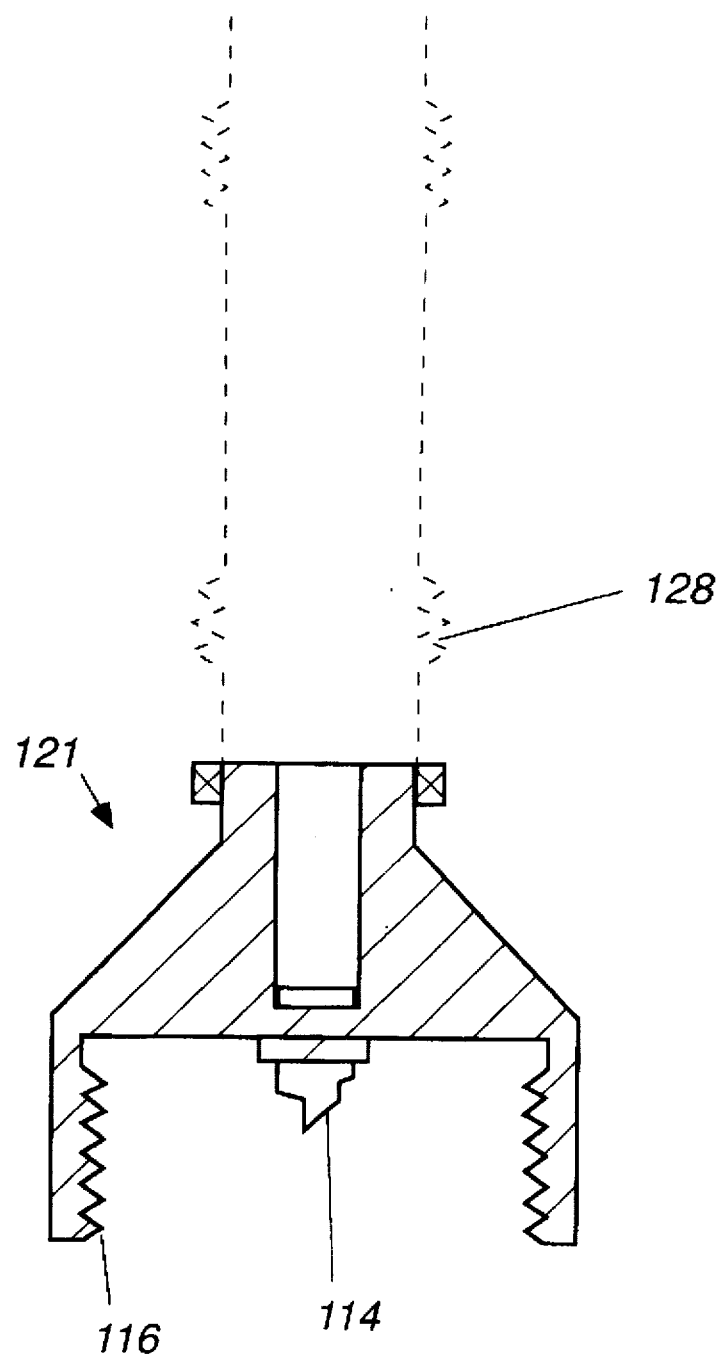
FIG. 22 shows a safety piercing attachment used with either the cap of FIG. 17 or FIG. 19 connected to a sterile plastic sheath.

Other variations of this generic connecting piece can also be utilized depending on particular need of the patient or desire of the treating physician. Two examples of the numerous combinations include, at FIG. 22, an attachment used to change the internal catheter 92, 110 while maintaining extremely sterile conditions. A guide wire 126 encased within a plastic sheath 128 is well known in the art. Here the plastic sheath 128 is connected to an independently rotatable cap attachment 121, similar to the one used for the medicinal bag of FIG. 21.

The guide wire 126 is inserted aseptically into the indwelling catheter 92, 110. Then the female connecting chamber 81, 108 is removed in tandem with the rotatable cap attachment 121 over the guide wire 126, leaving the guide wire 126 traversing the device 2, 50 in communication with the blood vessel. A new catheter 94, 110 can then be placed onto the guide wire 126 and into the vessel. The new female connecting chamber 81, 108 is then attached to the device 2, 50.

Figure 23A:
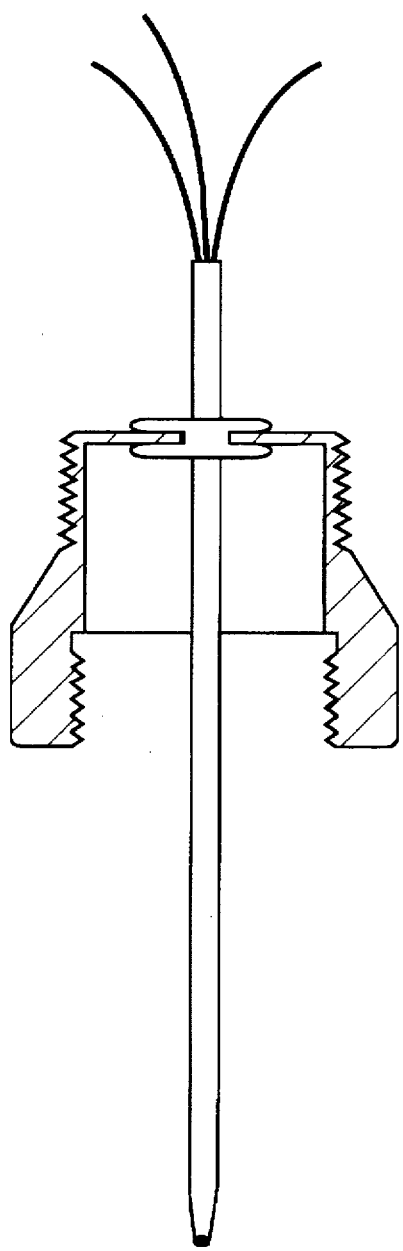
FIG. 23 shows a triple lumen variation of the caps illustrated in FIG. 17 and FIG. 19.
Figure 23B:
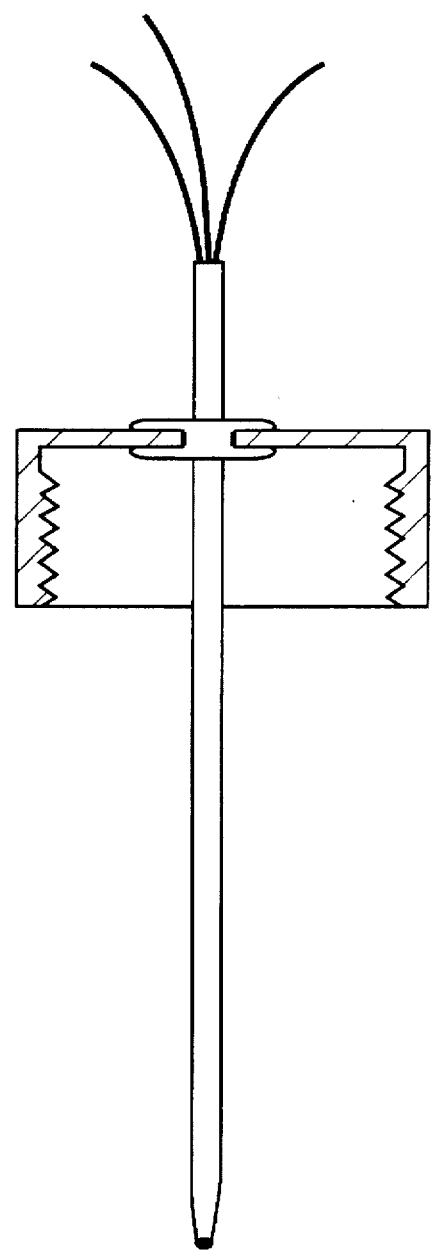

Further, FIGS. 23a and 23b show two caps, similar to those illustrated in FIGS. 17 and 19, which have triple lumen catheters rotatable connected thereto. These caps connect directly to the device and allow for multiple fluids to be introduced into the blood stream.

It is to be understood that the preceding descriptions are merely the preferred embodiments and that slight variations in structure or different combinations of components are within the contemplation of the inventor as well as the scope and spirit of the claims.

What is claimed is:

1. A catheter attaching device, comprising:

a body formed as a substantially inverted cone truncated near the vertex and having a central longitudinal bore;

a head having a central bore, said head being attached to one end of said body such that said central longitudinal bore and said central bore coincide to create an interior chamber;

an annular skin cup having a longitudinal bore coincidental with said interior chamber, and having at least two opposed faces, one of said faces being concave, said annular skin cup being integrally positioned between said head and said body, said;

means for initially puncturing skin, said puncturing means being slidably, rotatably and removably engaged within said interior chamber;

and securing means for securing said body to a puncture site created by said puncturing means, said securing means being integral with said body and formed as a substantially helical flange outwardly and radially extending from the outer face of said body, whereby constant rotation of said body causes said flange to increasingly engage said puncture site until said head contacts the exterior surface of said puncture site.

2. A catheter attaching device as recited in claim 1, wherein:

said head is threaded to accept a reversely threaded device.

3. A catheter attaching device as recited in claim 2, wherein:

said puncturing means is a trocar comprising a cylindrical body member having opposite ends and a longitudinal bore, one of said opposite ends having a handle, the other of said opposite ends having a cutting means and said longitudinal bore being sufficient in diameter to allow a surgical guide wire to be inserted therethrough.

4. A catheter attaching device, comprising:

a body having a central longitudinal bore;

a head having a central bore, said head being attached to one end of said body such that said central longitudinal bore and said central bore coincide to create an interior chamber;

means for initially puncturing skin, said puncturing means being slidably, rotatably and removably engaged within said interior chamber;

and securing means for securing said body to a puncture site created by said puncturing means, said securing means being a toggleable moly joint having a hollow central shaft, and at least two laterally opposed jointed and compressible members toggleable between two extreme positions, an insertion position and a locking position, whereby toggling of said moly joint results in displacement from one of said two extreme positions to the other of said two extreme positions.

5. A catheter attaching device as recited in claim 4, wherein:

said hollow central shaft is slidably positioned within said interior chamber such that said interior chamber and said hollow central shaft are longitudinally concentrically aligned with said puncturing means.

6. A catheter attaching device as recited in claim 5, further comprising:

an annular skin cup having a longitudinal bore, said annular skin cup being integrally positioned between said head and said body, said longitudinal bore being coincidental with said interior chamber.

7. A catheter attaching device as recited in claim 6, wherein:

said skin cup has at least two opposed faces, one of said faces being concave.

8. A catheter attaching device as recited in claim 7, wherein:

said head is threaded to accept a reversely threaded device.

9. A catheter attaching device as recited in claim 8, wherein:

said body is substantially a compressed inverted cone truncated near the vertex forming an annular end rim, said moly joint extending from said annular end rim and said central shaft traversing through said annular end rim.

10. A catheter attaching device as recited in claim 9, wherein:

said compressed inverted cone has a helical spiraling flange extending radially therefrom.

11. A catheter attaching device as recited in claim 10, wherein:

said central shaft has a distal and proximal end, said distal end having a helical spiraling flange extending radially therefrom.

12. A catheter attaching device as recited in claim 11, wherein:

said puncturing means is a trocar comprising a cylindrical body member having opposite ends and a longitudinal bore, one of said opposite ends having a handle, the other of said opposite ends having a cutting means and said longitudinal bore being sufficient in diameter to allow a surgical guide wire to be inserted therethrough.

13. A cap for a catheter attaching device, comprising:

a substantially hollow body having an inner surface defined by internal threads, an outer surface defined by external threads, a top opening and a bottom opening, a lumen having first and second ends, said first end being rotationally connected to said body and said second end extending through said bottom opening;

a self-sealing membrane covering said top opening of said body such that said membrane must be violated to gain access to said first end of said lumen, said membrane having a truncated conical insert protruding downwardly into said body to funnel fluids that traverse said membrane.

14. A cap for a catheter attaching device as recited in claim 13, wherein:

said rotational connection of said lumen and said body comprises a double flange on said lumen and a rigid cross section with an orifice within said body.

15. A cap for a catheter attaching device as recited in claim 3, further comprising:

substantially hollow body having an inner surface defined by internal threads, an outer surface defined by external threads, a top opening, and a bottom opening;

a lumen having first and second ends, said first end being rotationally connected to said body and said second end extending through said bottom opening;

a self-sealing membrane covering said top opening of said body such that said membrane must be violated to gain access to said first end of said lumen.

16. A cap for a catheter attaching device as recited in claim 12, further comprising:

a substantially hollow body having an inner surface defined by internal threads, an outer surface defined by external threads a top opening and a bottom opening;

a lumen having first and second ends, said first end being rotationally connected to said body and said second end extending through said bottom opening;

a self-sealing membrane covering said top opening of said body such that said membrane must be violated to gain access to said first end of said lumen.

* * * * *